United States Patent [19]
Fujieda et al.

[11] Patent Number: 6,033,075
[45] Date of Patent: Mar. 7, 2000

[54] OPHTHALMIC APPARATUS

[75] Inventors: Masanao Fujieda, Toyohashi; Yukinobu Ban, Nishio; Kan Otsuki, Toyokawa, all of Japan

[73] Assignee: Nidek Co., Ltd., Japan

[21] Appl. No.: 09/281,044

[22] Filed: Mar. 30, 1999

[30] Foreign Application Priority Data

| Mar. 31, 1998 | [JP] | Japan | 10-125442 |
| Mar. 31, 1998 | [JP] | Japan | 10-125445 |
| Jan. 28, 1999 | [JP] | Japan | 11-020781 |

[51] Int. Cl.$^7$ ........................................ A61B 3/10
[52] U.S. Cl. ........................ 351/212; 606/5; 606/166
[58] Field of Search ........................ 606/4, 5, 10, 13, 606/166; 351/200, 205, 212

[56] References Cited

U.S. PATENT DOCUMENTS

| 5,102,409 | 4/1992 | Balgorod | 606/5 |
| 5,500,697 | 3/1996 | Fujieda | 351/212 |
| 5,658,303 | 8/1997 | Koepnick | 606/166 |
| 5,713,893 | 2/1998 | O'Donnell, Jr. | 606/10 |
| 5,841,511 | 11/1998 | D'Souza et al. | 351/212 |

FOREIGN PATENT DOCUMENTS

| 0 836 830 | 4/1998 | European Pat. Off. . |
| 197 03 661 | 8/1997 | Germany . |
| 5-66125 | 9/1993 | Japan . |
| 7-124113 | 5/1995 | Japan . |
| 8-103413 | 4/1996 | Japan . |
| 8-280624 | 10/1996 | Japan . |
| 8-504108 | 12/1996 | Japan . |
| 9-266925 | 10/1997 | Japan . |
| 10-108837 | 4/1998 | Japan . |

OTHER PUBLICATIONS

Partial English translation of JP HEI 5-66125 (2 pages).
Partial English translation of JP HEI 8-103413 (5 pages).
U.S. application Ser No. 08/942,633.
U.S. application Ser No. 09/013,884.

*Primary Examiner*—George Manuel
*Attorney, Agent, or Firm*—Finnegan, Henderson, Farabow, Garrett & Dunner, L.L.P.

[57] ABSTRACT

An ophthalmic apparatus for calculating ophthalmic information of an eye to be operated, then determining an amount of corneal ablation for use in surgery for correcting ametropia, based on the calculated ophthalmic information, the apparatus comprising a first input device for inputting data of a pre-operative corneal shape obtained by corneal shape measurement, a second input device for inputting data of a pre-operative refractive power obtained by objective refractive power measurement, a first calculating device for calculating data of equivalent emmetropia corneal surface refractive power which is equivalent to cause the eye to be emmetropia, based on the data of the corneal shape and the data of the refractive power, a second calculating device for calculating estimation data of a post-operative corneal shape, based on the data of the equivalent emmetropia corneal surface refractive power, a third calculating device for calculating data of the amount of corneal ablation, based on the data of the pre-operative corneal shape and the data of the post-operative corneal shape, and a display device for displaying at least one of results calculated by the first, second and third calculating devices.

24 Claims, 6 Drawing Sheets

Equivalent size on a cornea

A calculated value of
a refractive power obtained by
a corneal shape measurement A calculated value of
a refractive power obtained by
a refractive power measurement

OPHTHALMIC APPARATUS

BACKGROUND OF THE INVENTION

1. Field of the Invention

The present invention relates to an ophthalmic apparatus, and more particularly, to the apparatus for obtaining ophthalmic information having relation to a refractive power and a corneal shape of an eye to be examined, and relates to the apparatus for determining an amount of corneal ablation, which is utilized for correcting ametropia in a manner of ablating a cornea thereby varying its corneal shape, based on the obtained ophthalmic information.

2. Description of Related Art

A refractive power of an eye to be examined, is obtained by using an objective refractive power measuring apparatus, or the like. For example, it is known for this apparatus which projects a measuring target onto a fundus of the eye, then detecting a reflex target image from the fundus thereby obtaining a refractive power. The refractive power reflects the ophthalmic information of a corneal region within 3 mm or less from a corneal center.

A corneal surface shape can be obtained by using a corneal curvature measuring apparatus, or a corneal shape analyzing apparatus. It is known for the corneal curvature measuring apparatus which detects a position of a measuring target being projected onto a cornea, thereby obtaining each curvature in directions of strong and weak principal meridians with defining a corneal shape as a toric. The value of the curvature is only for a corneal region within approximately 3 mm from a corneal center.

It is known for the corneal shape analyzing apparatus which gives an image processing to a numerous placido ring target and the like, projected onto a corneal surface, thereby obtaining distribution of a corneal curvature over a wide region of a cornea. Further, a corneal curvature is expressed in terms of a corneal refractive power. In general, the following expression (*) is used for this calculation.

$$D=(ne-1)/r \ldots (*)$$

Where, r is a corneal curvature, D is a refractive power, and ne is a corneal conversion rate. In general, a value of ne is 1.3375.

The value measured by the refractive power measuring apparatus denotes a refraction amount, i.e. a correcting amount, necessary for causing the eye to be emmetropia. Thus, it differs from the value D obtained from the expression (*) in its true sense. Therefore, the value obtained by each measuring apparatus is handled with under the definition that each value is different one. The relationship among each value is difficult to understand.

Further, it is known for an apparatus for operating upon a cornea, which ablates a corneal surface or its stroma with a laser beam, thus causing a corneal surface shape to vary, thereby correcting ametropia of an eyeball. In this surgical operation, the apparatus obtains a pre-operative corneal shape and its refractive power, thereby calculating an amount of corneal ablation necessary for correction. In the past, this calculation is performed as following.

Firstly, a corneal shape is assumed based on an average of a pre-operative corneal curvature obtained by a corneal curvature measurement, on the assumption that a corneal surface of an eye to be operated is spherical or toric. In the assumption, S (a spherical power), C (a cylindrical power) and A (an astigmatic axial angle) are used, the values S, C and A being obtained by a subjective refractive power measurement or an objective refractive power measurement. Then, an amount of corneal ablation is calculated on the assumption as following: a spherical surface or a toric surface which are formed by a corneal stroma is to be ablated; the values S, C and A may be corrected (or calibrated); and a post-operative corneal shape is also to be a spherical surface or a toric surface.

However, a cornea of a human eye does not always have a spherical surface or a toric surface, thus there are some cases that a corneal shape is non-symmetric. Because, a corneal surface shape is different in part due to irregular astigmatism or the like. In addition, a refractive power is not always symmetric with respect to a corneal center. In the prior art, an objective refractive power measurement apparatus only calculates the values S, C and A (these values represent a spherical surface or a toric surface), obtained by measuring a limited region within 3 mm or less from a corneal center. It is insufficient to determine an amount of corneal ablation based on the values S, C and A.

Provided that a human eye is a system of an image optics from a cornea to a retina, spherical aberration has influence upon the above described ablation that causes a post-operative corneal shape to be spherical or toric. In this point of view, the ablation in the prior art is also insufficient. Intrinsically, a corneal surface of a human eye is not spherical, there is possibility that the ablation in the prior art has bad influence upon aberration.

SUMMARY OF THE INVENTION

The present invention has been made in view of the above circumstances and has an object to overcome the above problems and to provide an ophthalmic apparatus which can calculates relationship between a refractive power and a corneal shape in the plain form.

Another object of the present invention is to provide an ophthalmic apparatus and that utilized for operating upon a cornea, which can determine an amount of corneal ablation in accordance with condition of a corneal shape and a refractive power of the eye to be operated, and can be used for obtaining a preferable correction result.

Further, another object of the present invention is to provide an ophthalmic apparatus and that utilized for operating upon a cornea, which can determine an amount of corneal ablation so that a corneal shape may be non-spherical shape and influence due to spherical aberration may be decreased.

To achieve the objects and in accordance with the purpose of the present invention, as embodied and broadly described herein, an ophthalmic apparatus for calculating ophthalmic information of an eye to be operated, then determining an amount of corneal ablation for use in surgery for correcting ametropia, based on the calculated ophthalmic information, the apparatus comprises a first input device for inputting data of a pre-operative corneal shape obtained by corneal shape measurement; a second input device for inputting data of pre-operative refractive power obtained by objective refractive power measurement; a first calculating device for calculating data of equivalent emmetropia corneal surface refractive power which is equivalent to cause the eye to be emmetropia, based on the data of the corneal shape inputted by the first input device and the data of the refractive power inputted by the second input device; a second calculating device for calculating estimation data of a post-operative corneal shape, based on the data of the equivalent emmetropia corneal surface refractive power calculated by the first calculating device; a third calculating device for calculating data of the amount of corneal ablation, based on the data of the corneal shape inputted by the first input device and the data of the corneal shape calculated by the second calculating device; and a display device for displaying at least one of results calculated by the first, second and third calculating devices.

Another aspect of the present invention, an ophthalmic apparatus for calculating ophthalmic information, the apparatus comprises an input device for inputting data of corneal surface refractive power obtained by corneal shape measurement and data of refractive power obtained by objective refractive power measurement; a calculating device for calculating data of equivalent emmetropia corneal surface refractive power which is equivalent to cause the eye to be emmetropia in a manner of adding the data of the corneal surface refractive power and the data of the refractive power, both data being inputted by the input device; and a display device for displaying a result calculated by the calculating device.

Further, another aspect of the present invention, an ophthalmic apparatus for determining an amount of corneal ablation for use in surgery for correcting ametropia in a manner of ablating a cornea, the apparatus comprises a first input device for inputting distribution data of a pre-operative corneal curvature obtained by corneal shape measurement; a second input device for inputting distribution data of pre-operative refractive power obtained by objective refractive power measurement; and an ablation amount calculating device for calculating data of the amount of corneal ablation, based on the distribution data of the corneal curvature inputted by the first input device and the distribution data of the refractive power inputted by the second input device.

Further, another aspect of the present invention, an ophthalmic apparatus for determining an amount of corneal ablation for use in surgery for correcting ametropia in a manner of ablating a cornea, the apparatus comprises an input device for inputting data of a pre-operative corneal curvature obtained by corneal shape measurement and data of pre-operative refractive power obtained by refractive power measurement; and a calculating device for calculating data of the amount of corneal ablation, which causes a corneal surface to be non-spherical shape such that influence of aberration is eliminated, based on the data inputted by the input device.

Further, another aspect of the present invention, an ophthalmic apparatus utilized for surgery for correcting ametropia in a manner of ablating a cornea, the apparatus comprises a first input device for inputting distribution data of a pre-operative corneal curvature, obtained by corneal shape measurement; a second input device for inputting distribution data of pre-operative refractive power, obtained by objective refractive power measurement; a calculating device for calculating data of an amount of corneal ablation, based on the distribution data of the corneal curvature inputted by the first input device and the distribution data of the refractive power inputted by the second input device; and an ablation device for ablating the cornea with a laser beam, based on the data of the amount of corneal ablation calculated by the calculating device.

Further, another aspect of the present invention, an ophthalmic apparatus utilized for surgery for correcting ametropia in a manner of ablating a cornea, the apparatus comprises an input device for inputting data of a pre-operative corneal shape obtained by corneal shape measurement and data of pre-operative refractive power obtained by refractive power measurement; a calculating device for calculating data of an amount of corneal ablation, which causes a corneal surface to be non-spherical shape such that influence of aberration is eliminated, based on the data inputted by the input device; and an ablation device for ablating the cornea with a laser beam, based on the data of the amount of corneal ablation calculated by the calculating device.

According to the present invention, relationship between a refractive power and a corneal shape can be obtained in the plain form. Thereby, appropriate diagnosis can be made, and appropriate correction of ametropia can be made.

Further, an amount of corneal ablation can be determined in accordance with a corneal shape and a refractive power of the eye to be operated, and can be used for obtaining a preferable correction result.

In addition, the correction effect by the present invention may be improved compared with that in the prior art, in a manner of ablating a corneal surface so that influence due to aberration may be decreased.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
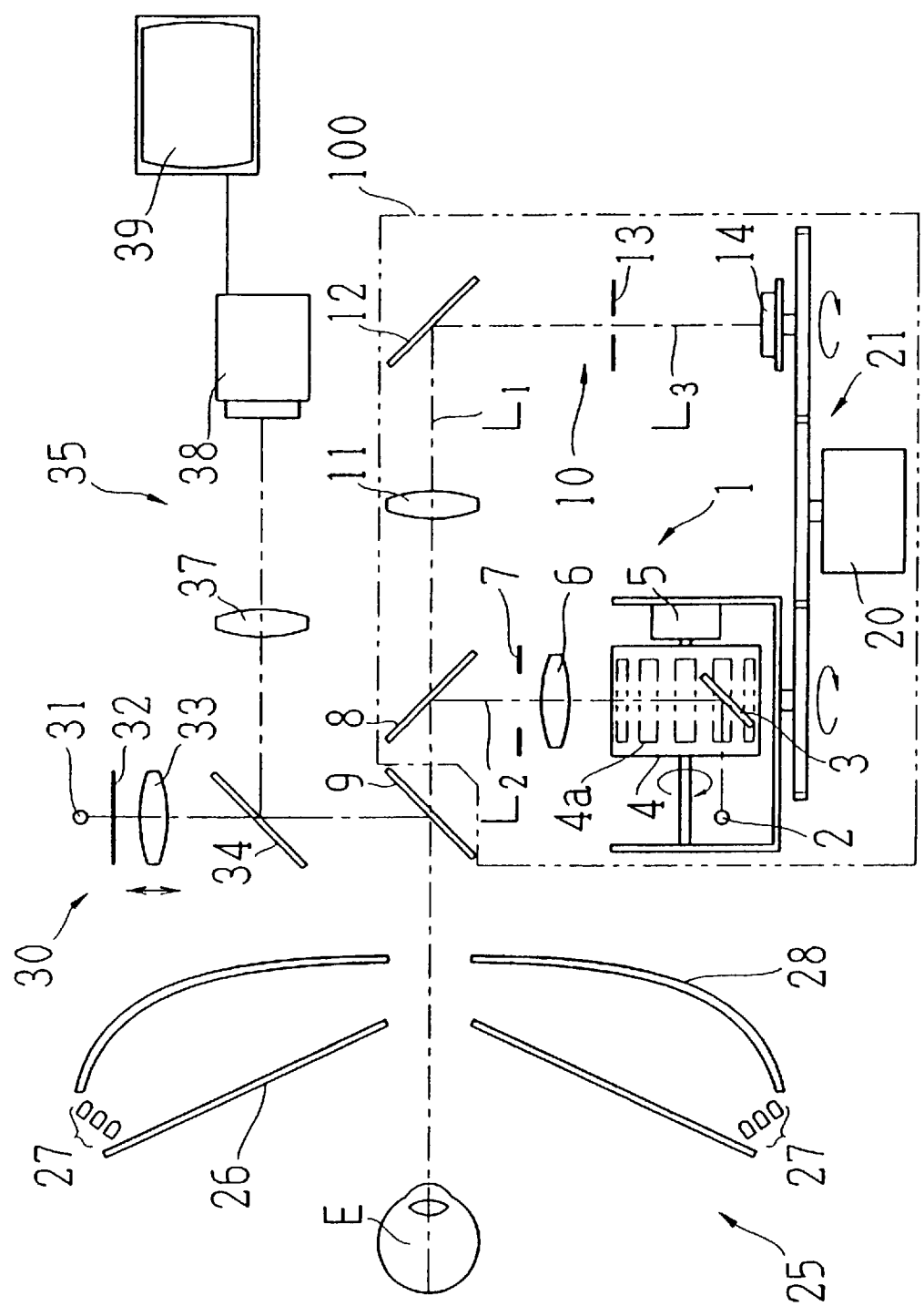
FIG. 1 is a view showing a schematic arrangement of an optical system of the preferred embodiment of the present invention.

A detailed description of one preferred embodiment of the present invention will now be given referring to the accompanying drawings. FIG. 1 is a view showing a schematic arrangement of an optical system of the preferred embodiment of the present invention. The optical system is roughly divided into a refractive power measuring optical system, a fixation target projecting optical system and a corneal curvature measuring optical system.

Refractive Power Measuring Optical System

The refractive power measuring optical system 100 includes a slit projecting optical system 1 and a slit-image detecting optical system 10. A light within a range of near infrared rays from a light source 2 of the projecting optical system 1 is reflected by a mirror 3, then illuminating a slit aperture 4a of a rotation sector 4. Driven by a motor 5, the rotation sector 4 rotates. A slit light bundle, scanned by a rotation of the sector 4, passes through a projecting lens 6 and a limit diaphragm 7, then being reflected by a beam splitter 8. The slit light bundle then transmits a beam splitter 9 which makes the optical axis of the fixation target projecting optical system and that of the observation optical system (details are described below) coaxial, then converging in the vicinity of a cornea of an eye E and being projected onto a fundus thereof. The light source 2 is disposed at the conjugate position with the vicinity of the cornea of the eye E with respect to the projecting lens 6.

Figure 2:
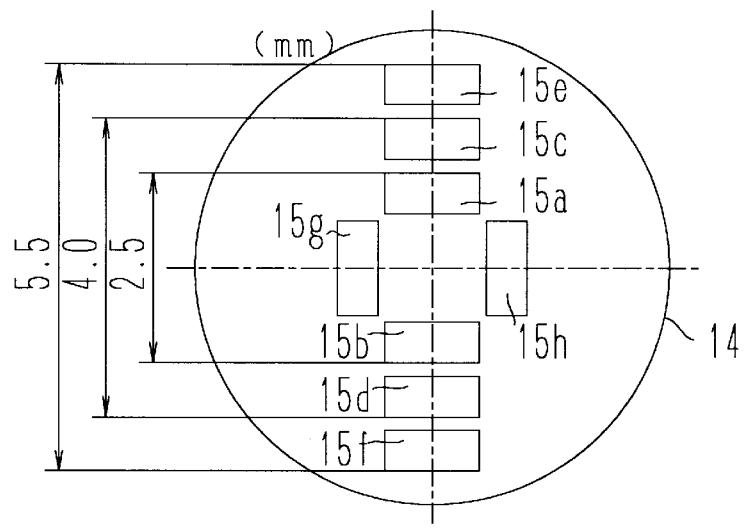
FIG. 2 is a view showing an arrangement of photo-detectors provided for a photo-receiving part.

The slit-image detecting optical system 10 is provided with a photo-receiving lens 11 and a mirror 12, arranged on the principal optical axis L1, and a diaphragm 13 and a photo-receiving part 14, arranged on the optical axis L3. Where, the optical axis L3 is formed by reflection of the mirror 12. The diaphragm 13 is positioned at the back focal point of the lens 11 via the mirror 12 (that is, at the conjugate position with a fundus of the eye having emmetropia). As shown in FIG. 2, eight photo-detectors 15a–15h are disposed on the surface of the photo-receiving part 14 so as to be at approximately the conjugate positions with the cornea of the eye E with respect to the lens 11. Six photo-detectors 15a–15f out of eight photo-detectors 15a–15h are positioned on the line passing through the center (i.e., the optical axis L3) of the photo-receiving surface, so as to make pairs, 15a with 15b, 15c with 15d, and 15e with 15f. Respective pairs are symmetric with respect to the center of the photo-receiving surface. The configuration distance of these three pairs is set so as to detect a refractive power corresponding to respective positions in the meridian direction of the cornea (in FIG. 2, it is shown as an equivalent size on the cornea). In contrast, the photo-detectors 15g and 15h are positioned on the line perpendicular to the line passing through the photo-detectors 15a–15f with the center at the optical axis L3, so as to be symmetric with respect to the center (i.e., the optical axis L3) of the photo-receiving surface.

In the measuring optical system 100 having above-described construction, a rotation mechanism 21 comprising a motor 20, a gear and the like rotates the components of the slit projecting optical system 1, such as the light source 2, the mirror 3, the sector 4 and the motor 5, on the optical axis L2, and also rotates the photo-receiving part 14 on the optical axis L3 with making the rotations synchronized to each other. In the preferred embodiment, the photo-detectors 15a–15f are disposed in the direction perpendicularly intersecting the long side of the slit received by the photo-receiving part 14, in the case that a slit light bundle caused by the aperture 4a is scanned on a fundus of the eye having hyperopia or myopia exclusive of astigmatism.

Fixation Target Projecting Optical System 30 is a fixation target projecting optical system, 31 is a visible light source, 32 is a fixation target and 33 is a projecting lens. The lens 33 moves toward the optical axis, thereby fogging the eye E. 34 is a beam splitter which makes an optical axis of the observation optical system coaxial. The light source 31 illuminates the fixation target 32, from which the light bundle passes through the lens 33 and the beam splitter 34, then being reflected by the beam splitter 9 thereby reaching to the eye E. The eye E is fixed on the fixation target 32.

Corneal Curvature Measuring Optical System

A corneal curvature measuring optical system includes a target projecting optical system 25 for measuring a curvature and a target detecting optical system 35 for measuring a curvature. The projecting optical system 25 has below mentioned configuration. 26 is a conic placido-plate provided with an aperture in the center thereof, and there formed ring patterns having a numerous light intercepting part and light passing part on concentric circles with the center on the optical axis L1. 27 is a plurality of illumination light sources, such as LED or the like, the illumination light therefrom is reflected by a reflecting plate 28, so as to illuminate the placido-plate 26 from behind almost evenly. The light bundle having a ring pattern, passed through the light passing parts of the placido-plate 26, is projected onto the cornea of the eye E.

The detecting optical system 35 includes the beam splitter 9, the beam splitter 34, a photographing lens 37 and a CCD camera 38. A light bundle of the corneal reflection having ring patterns projected by the projecting optical system 25 is reflected by the beam splitter 9 and the beam splitter 34 in succession, then forming an image of the corneal reflection having ring patterns on the surface of the photographing elements of the CCD camera 38 by the lens 37. In addition, the detecting optical system 35 also acts as an observation optical system. An image of an anterior portion of the eye E illuminated by an illumination light source, not shown, forms an image on the surface of the photographing elements of the CCD camera 38, then being displayed on the TV monitor 39.

Figure 3:
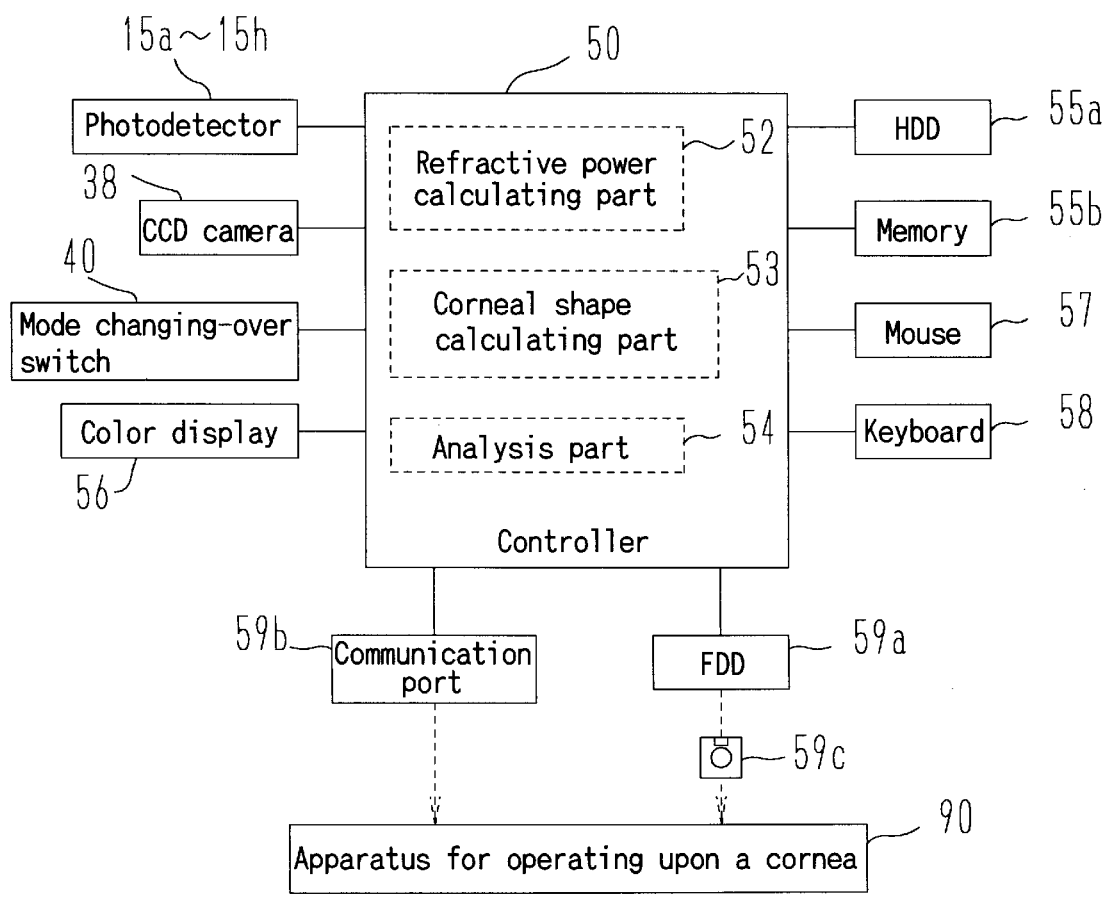
FIG. 3 is a view showing a schematic construction of a control system of the preferred embodiment of the present invention.

Next, the operation of the apparatus having above mentioned architecture will be described hereinafter with referring to the block diagram of the control system shown in FIG. 3. Firstly, the measurement of a refractive power and that of a corneal curvature will be described.

In the case of measuring a corneal curvature, the operator selects the mode for measuring a corneal curvature by using a mode changing-over switch 40. The operator performs alignment with observing the image of the anterior portion of the eye E displayed on the monitor 39, which is illuminated by the anterior portion illumination light source. A well known manner can be used for the alignment. The manner is such that a target for positional adjustment is projected on a cornea, then a corneal reflecting luminous point and a reticle are made to have predetermined relationship. After completing alignment, the operator pushes a start switch for the measurement, not shown, thereby a trigger signal being generated, responding to which, the measurement is made to be started.

Figure 4:
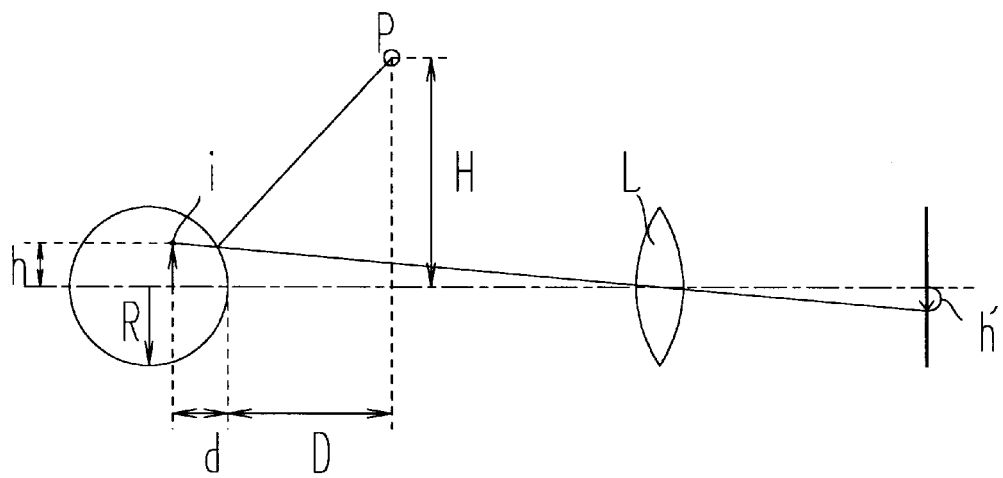
FIG. 4 is a view for illustrating a method of calculating a corneal curvature.

A corneal shape calculating part 53 detects an edge of an image of a placido-ring (ring pattern) by processing an image photographed by the CCD camera 38. Then, the calculating part 53 calculates a corneal curvature by obtaining each edge position relative to a corneal center at intervals of a predetermined angle (1°). The calculation for obtaining a corneal curvature can be carried out as follows. As shown in FIG. 4, the detected height is defined as h' at the time when an image i due to the corneal convex surface of the light source P at the distance D on the optical axis and the height H from the cornea is formed on the two-dimensional detecting plane by the lens L. And the magnification of the optical system of the apparatus is defined as m. The corneal curvature radius R is given by following expression:

$$R=(2D/H)mh'$$

It is also possible to adapt a method of calculating a corneal curvature as follows. The curvature radius of the region where the j-th ring is projected onto the cornea is defined as Rj. The proportional constant which is determined by the height of the j-th ring, the distance up to the eye E and the photographing magnification is defined as Kj. The image height on the photographing plane is defined as hj. The relationship expression as identified above is given by following expression:

$$Rj = kj \cdot hj$$

Where, if a plurality of model eyes having different curvatures which cover the measurement range is measured in advance, then the proportional constant Kj is obtained as an intrinsic value for the apparatus. Therefore, if the constant Kj is read out and utilized for calculation at the time of measuring, then the distribution of the corneal curvature is obtained in extremely short time. The details of this calculation, see U.S. Pat. No. 5,500,697 corresponding to the Japanese Patent Publication Laid-Open No. HEI 7(1995)-124113. The obtained data of the corneal curvature is stored in a memory 55b.

In the case of measuring a refractive power of the eye (it is referred to as an objective refractive power), the operator changes the mode to the mode for measuring a refractive power (in the case of the continuous measurement mode, it is automatically changed to the mode for measuring a refractive power), then the measurement is performed by the measuring optical system 100. The refractive power calculating part 52 obtains distribution of an objective refractive power, based on each phase difference of output signals from each photo-detector of the photo-receiving part 14. Firstly, the preliminary measurement is performed by a similar method of measuring a refractive power in the prior art. Based on its result, the eye E is fogged by moving the lens 33 in the fixation target projecting optical system 30. Thereafter, the corneal center is calculated in a meridian direction where the photo-detectors 15a–15f are placed. This calculation is based on signals outputted from the photo-detectors 15g and 15h, the signals varying in accordance with movement of light caused by a slit image on the photo-receiving part 14. Next, based on a phase difference between each signal outputted from each photo-detector 15a–15f and the corneal center, a refractive power at a corneal part corresponding to each photo-detector is calculated. This calculation for obtaining the refractive power every meridian of each axial step, under the condition that the projecting optical system 1 and the photo-detector 14 are made to be rotated 180° around the optical axis at a predetermined angle, such as 1° (in details, see a Japanese Patent Publication Laid-Open No. HEI10(1998)-108837 corresponding to U.S. application Ser. No. 08/942,633 and EP Publication No. 0836830). The calculated value of the refractive power is obtained on the assumption that a corneal vertex is defined as a standard (the apparatus can also output a value of a refractive power, with defining a position where a pair of spectacles is worn as a standard value). The obtained data of the objective refractive power is stored in a HDD 55a or a memory 55b.

If the measured data both of an objective refractive power and a corneal curvature are obtained as above described, then the operator operates a keyboard 58 and a mouse 57 in accordance with an instruction displayed on a color display 56, connected to a control part 50, thereby causing analysis to start. The analysis part 54 provided for the control part 50 converts the corneal curvature into a corneal surface refractive power, then executing an analysis program. This analysis program is utilized for obtaining relationship between the objective refractive power and the converted corneal surface refractive power.

Next, a method of converting the corneal curvature into the corneal surface refractive power. The corneal surface refractive power is such power that is obtained when a light bundle parallel to a normal line of a corneal vertex is refracted by the cornea. When converting the corneal curvature into the corneal surface refractive power, the Snell's law (or it is called the law of refraction) is used. In the conversion, the above identified expression (*) can be applied to the vicinity of the measuring optical axis (the vicinity of a corneal center) because of its little error. However, the expression (*) can be applied only to the vicinity of the measuring optical axis. If the expression (*) is applied to the corneal periphery wider than the vicinity, then reliability is lowered. In the case of treating the periphery region of the cornea, such definition is made that a light entering into the cornea shows refraction based on the Snell's law. The refractive power obtained under this definition is comparable with the objective refractive power under the same scale. In addition, the Snell's law defines that a normal line at an entering point of a light beam and a light beam refracted at this entering point are on the same plane at the time when the light beam enters into a refraction plane, and further defines that a ratio of a sin value of an angle formed by a normal line and a refracted light beam relative to a sin value of an angle formed by a normal line and an entering light beam is a constant. The Snell's law is given by following expression:

$$N \sin i = N' \sin i'$$

Where, each refractive index at each side of a refraction plane is defined as N and N'. And an angle formed by an entering light beam and a normal line is defined as i, and an angle formed by a refracted light beam and a normal line is defined as i'.

Figure 5:
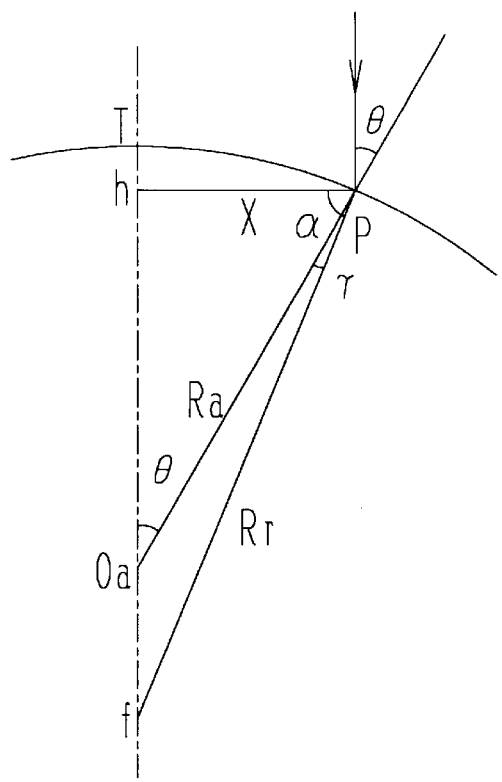
FIG. 5 is a view for illustrating a method of calculating a corneal surface refractive power.

Next, the calculation of the corneal surface refractive power by using the Snell's law will be described hereinafter. In FIG. 5, a light parallel to a line passing through a corneal vertex T and a curvature center $O_a$ is defined as to refract at a point P on the cornea, where is X distance from the corneal vertex T, and is defined as to intersect at a point f with a line $TO_a$. Where, following definition is given (a unit of a distance is a meter):

$R_a$: a corneal curvature at a point P $R_r$: a distance from a point P to a point f (meter)

θ: an angle between a normal line at a point P and an incidence light

γ: an angle between a normal line at a point P and a refracted light

A refractive power at a point P can be calculated by following calculation steps.

Firstly, as shown in FIG. 5, the angle θ is given by following expression:

$$\theta = \sin^{-1}\left(\frac{x}{R_a}\right) \quad (1)$$

Next, the angle γ is given by following expression based on the Snell's law:

$$\gamma = \sin^{-1}\left(\frac{x}{R_a \times n}\right) \quad (2)$$

Based on the expressions (1) and (2), an angle α (an angle formed by a segment hP and a segment Pf), a distance $R_r$, and a segment hf are given by following expressions:

$$\alpha = 90 - \theta + \gamma \quad (3)$$

$$R_r = \frac{x}{\cos(\alpha)}$$

$$\overline{hf} = \sqrt{R_r^2 - x^2}$$

In addition, a distance of a segment Th is given by following expression:

$$\overline{Th} = R_a - \sqrt{R_a^2 - x^2} \quad (4)$$

Accordingly, a distance from the corneal vertex T to the point f is given by following expression:

$$\overline{Tf} = \overline{Th} + \overline{hf} = R_a - \sqrt{R_a^2 - x^2} + \sqrt{R_r^2 - x^2} \quad (5)$$

A refractive power Dc in a cornea of which a refractive index n equals to 1.376 is given by following expression:

$$Dc = \frac{1}{\overline{Tf}} = \frac{1}{R_a - \sqrt{R_a^2 - x^2} + \sqrt{R_r^2 - x^2}} \quad (6)$$

In contrast, a refractive power D in air is given by following expression:

$$D = n \times Dc = \frac{n}{R_a - \sqrt{R_a^2 - x^2} + \sqrt{R_r^2 - x^2}} \quad (7)$$

If the calculation by using the above identified expressions (1) to (7) is performed with respect to all measuring region, then the corneal surface refractive power is calculated. Alternatively, the calculation may be performed by the corneal shape calculating part 53.

Next, the objective refractive power is then converted to a refractive power equivalent to a corneal surface with respect to the corneal surface refractive power calculated as described above. The converted value results in the form of a corneal surface refractive power necessary for causing the eye E to be emmetropia (in this specification, this is referred to as "an equivalent emmetropia corneal surface refractive power").

Figure 6A:
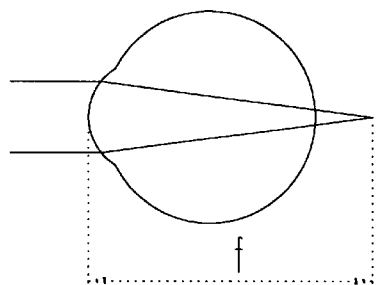
FIGS. 6A and 6B are views showing difference between a calculated value of a refractive power obtained by measuring a corneal shape and a measured value obtained by an objective refractive power measurement.
Figure 6B:
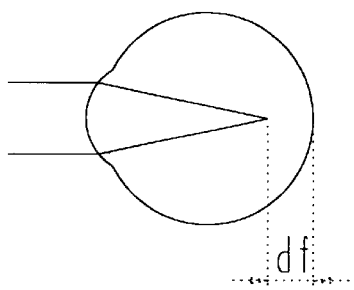

Here, the relationship between the objective refractive power and the corneal surface refractive power obtained from a corneal shape is as follows. As shown in FIG. 6, the meanings of a value of the objective refractive power differs entirely from a value of the corneal surface refractive power obtained from a corneal shape. The refractive power obtained from a corneal shape is obtained by calculating a focal distance f, then converting it. In contrast, the objective refractive power is obtained by measuring a refractive power (correcting amount) df necessary for causing the eye to be emmetropia. For example, if the corneal surface refractive power obtained from a corneal shape is 43.50 D and the objective refractive power measured is 0 D (both values are of the same corneal region), then the eye E proves to have such optical system that forms an image on a retina when the corneal surface refractive power is 43.50 D. If the corneal surface refractive power obtained from a corneal shape is 43.50 D and the objective refractive power is −2 D, then the eye E proves to be in need of correction of the corneal surface refractive power of an amount of −2 D (41.50 D) to form an image on the retina.

Accordingly, in the region where the objective refractive power is measured, a corneal surface refractive power which causes the eye to be emmetropia is calculated in a manner of adding the measured objective refractive power including a sign and the corneal surface refractive power obtained from the corneal shape measurement. The calculated value proves to be the equivalent emmetropia corneal surface refractive power, being given by following expression:

An equivalent emmetropia corneal surface refractive power = A corneal surface refractive power + An objective refractive power In addition, the equivalent emmetropia corneal surface refractive power can be converted into the corneal curvature, based on the Snell's law. This conversion can be performed by using the below identified two expressions found by the same way as shown in FIG. 5:

$$R_r = \frac{R_a}{\sqrt{1 - \left(\frac{x}{n \times R_a}\right)^2} - \frac{1}{n}\sqrt{1 - \left(\frac{x}{R_a}\right)^2}} \quad (8)$$

$$\sqrt{R_r^2 - x^2} + R_a - \sqrt{R_a^2 - x^2} - \frac{n}{D} = 0$$

Where, D is defined as the equivalent emmetropia corneal surface refractive power; Ra is the solved corneal curvature, denoting an estimation shape of a post-operative corneal shape.

By using the equivalent emmetropia corneal surface refractive power D and the corneal curvature Ra converted, relationship between the value of the objective refractive power and the value obtained from the corneal shape measurement can be expressed in the form of the corneal surface. Thereby, the relationship can be utilized for estimating the corneal surface shape. In general, it is said that a total refractive power of an eye is a sum of a corneal refractive power and a lens refractive power, it is not easy to know a lens refractive power. Additionally, an ocular axial length is also a cause of ametropia. In contrast, the above identified expressions enables the operator to know relationship between the refractive power of an eye and the corneal surface shape by replacing ametropia with a corneal surface shape, even if the operator does not know unknown values, such as a lens refractive power, an ocular axial length and the like.

Figure 7:
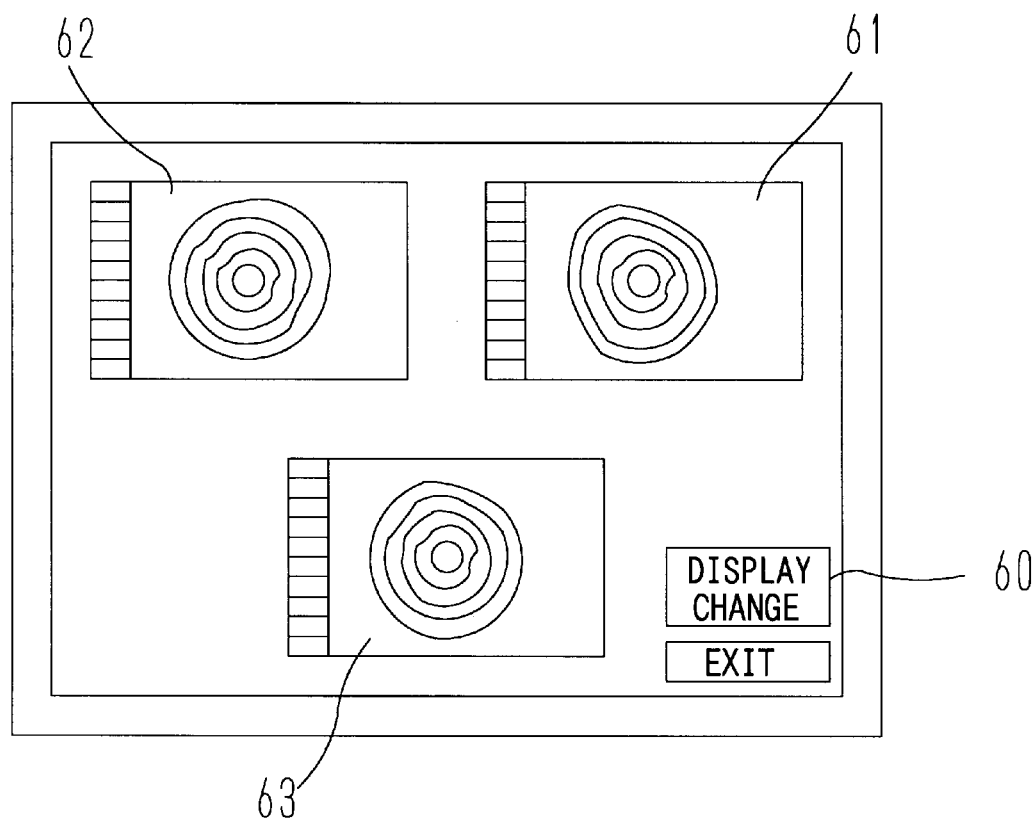
FIG. 7 is a view showing an example of a color map.

As above described, the equivalent emmetropia corneal surface refractive power (and the corneal curvature converted) is obtained, then the equivalent emmetropia corneal surface refractive power, the objective refractive power and the corneal surface refractive power are visually displayed on the display 56 so as to be compared easily with each other. FIG. 7 is an example of a color map. Distribution of the corneal surface refractive power obtained from the corneal shape measurement is displayed on a display part 61 at a right upper part of the display 56; distribution of the objective refractive power is displayed on a display part 62 at a left upper part thereof; distribution of the equivalent emmetropia corneal surface refractive power is displayed on a display part 63 at a lower part thereof. Each distribution is displayed in the form of a color map. In addition, the display can be changed-over with a display changing key 60 at a right lower part of the display 56. The corneal curvature obtained from the corneal curvature measurement and the corneal curvature obtained by converting the equivalent emmetropia corneal surface refractive power can be displayed in several manners such as a color map, a three-dimensional picture, or a superposed picture formed by three-dimensional sectional pictures in a certain meridian direction.

As described above, relationship among the measured result of the objective refractive power, the measured result of the corneal shape and the equivalent emmetropia corneal surface refractive power obtained from these results are graphically displayed. The operator can grasp variation of pre- or post- operative corneal refractive power and corneal shape visually in the case of surgery for correcting upon a cornea, which causes an eye to be emmetropia.

Further, if an instruction is given in response to operation of the mouse 57, then an analysis program for use in surgery for correcting upon a cornea is executed. Thereby, the analysis part 54 calculates an amount of corneal ablation, based on the corneal curvature obtained by converting the equivalent emmetropia corneal surface refractive power and the corneal curvature obtained by the corneal shape measurement. This calculation method will be described hereinafter.

Figure 8A:
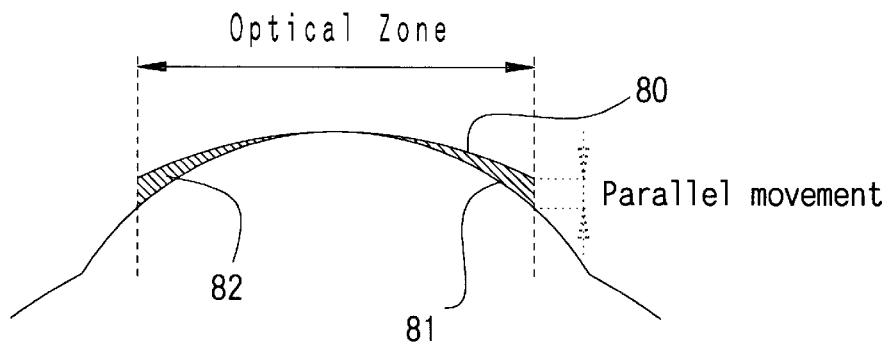
FIGS. 8A and 8B are views for illustrating an amount of corneal ablation in the case of myopia correction.
Figure 8B:
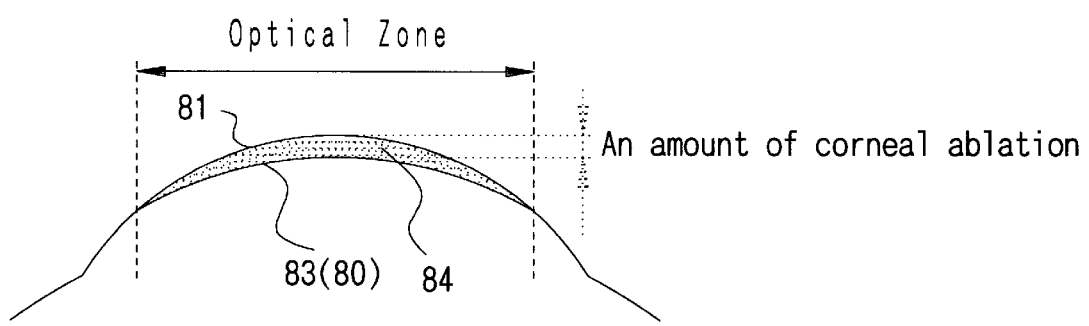
Figure 9:
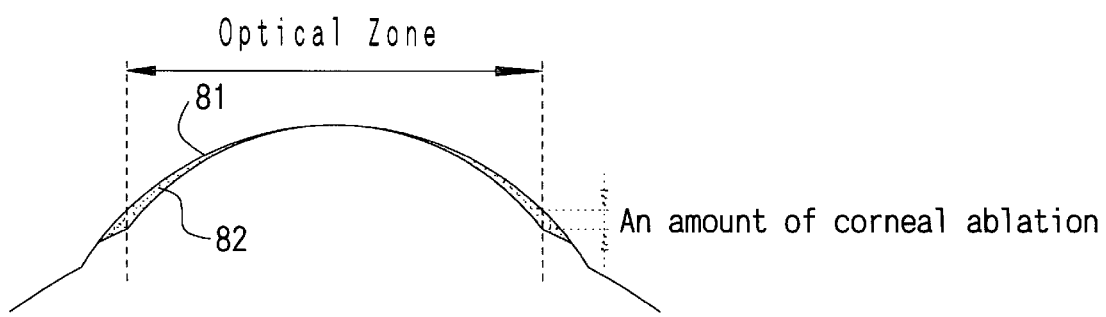
FIG. 9 is a view for illustrating an amount of corneal ablation in the case of hyperopia correction.

As shown in FIGS. 8 and 9 (to make description simple, a corneal shape is defined as a circle, being shown as a sectional plane in a certain meridian direction), in an optical zone which denotes an ablation region, a three-dimensional shape (a 3-D shape) 80 is calculated, based on the corneal curvature obtained by converting the equivalent emmetropia corneal surface refractive power. Then, based on this 3-D shape 80 and the 3-D shape 81 based on the corneal curvature obtained by the corneal shape measurement, distribution of height difference 82 in the optical zone is calculated with defining a corneal vertex as a standard.

In the case of myopia correction, as shown in FIG. 8B, the central part of the cornea is deeply ablated, thereby the corneal curvature being made to be large. Therefore, the 3-D shape 80 obtained from the equivalent emmetropia corneal surface refractive power is made to move toward a lower direction by parallel movement by a maximum amount of the height difference between two 3-D shapes 80 and 81. The 3-D shape 83 after this movement proves to be the corrected corneal surface, which causes the eye to be emmetropia. Distribution of difference 84 between the 3-D shape 81 obtained by the corneal shape measurement and the 3-D shape 83 (80) after movement obtained from the equivalent emmetropia corneal surface refractive power proves to be information of the amount of corneal ablation. (A maximum amount having an effect on refractive error due to variation of an ocular axial length after ablation is approximately 0.25 D, thereby the amount being ignored.)

In contrast, in the case of hyperopia correction, as shown in FIG. 9, the periphery of the cornea is deeply ablated, thereby causing the corneal curvature to be small. In this case, distribution of height difference 82 between two 3-D shapes 80 and 81 proves to be information of the amount of corneal ablation, with respect to all region of the optical zone.

Additionally, in either case identified above, in the case that the maximum amount of corneal ablation excesses the allowable amount of corneal ablation with respect to all region of the optical zone, then the amount of corneal ablation is corrected by causing the optical zone to be small so as to be within the allowable amount. In the case that the amount of corneal ablation denotes negative sign due to unevenness, then whole amount of corneal ablation is controlled.

Information of the amount of corneal ablation can be obtained by several methods, such as above described method which calculates distribution of the amount of corneal ablation based on difference between both 3-D shapes, a method which uses distribution information of the objective refractive power.

For example, a plurality of regions of concentric circles from a central region to a periphery region in optical zone are set with respect to distribution of the corneal curvature obtained by the corneal shape measurement and distribution of the corneal curvature obtained from the equivalent emmetropia corneal surface refractive power. Then, approximation is given to the corneal curvature every each region of each concentric circle. From which, a 3-D shape is obtained, then distribution of the amount of corneal ablation is calculated (it is desirable that each boundary is adjusted so as to follow smoothly). This method improves correction accuracy at the periphery region by way of a relative easy laser beam control method, compared with the ablation method which defines an ablation region in a whole optical zone as uniform spherical or toric surface.

In addition, information of the amount of corneal ablation can be obtained in a manner of dividing the corneal shape obtained by the corneal shape measurement and the corneal shape obtained from the equivalent emmetropia corneal surface refractive power into a plurality of regions respectively, thereby causing respective corneal shapes to be non-spherical shapes which can be expressed by the calculating formula.

By performing corneal ablation surgery based on information of an amount of corneal ablation obtained as described above, a correction result better than a prior art may be obtained. That is, in general, although a corneal shape of a human eye is a non-spherical shape, a corneal ablation in the prior art was based on a method which defines a cornea as a spherical surface (or a toric surface). Referring to the method of the present invention, however, a non-spherical surface may be kept automatically. That is, referring to the present invention, such condition can be ensured that influence of spherical aberration is eliminated, accordingly only a component of ametropia can be ablated with keeping an original corneal shape.

Data of the amount of corneal ablation, calculated by the analysis part 54, is stored into the HDD 55a or the memory 55b. This data is transferred to the apparatus 90 for operating upon a cornea, which ablates a cornea by an excimer laser beam via a communication cable, connected to FD 59c driven by the floppy disc drive (FDD) 59a and the communication port 59b. The apparatus 90 determines a number of irradiation pulses and an irradiation power on each coordinates of the cornea, based on the inputted data of the amount of corneal ablation. In accordance with the determined values, the apparatus 90 carries out surgery for operating upon a cornea by controlling a laser irradiation.

Figure 10:
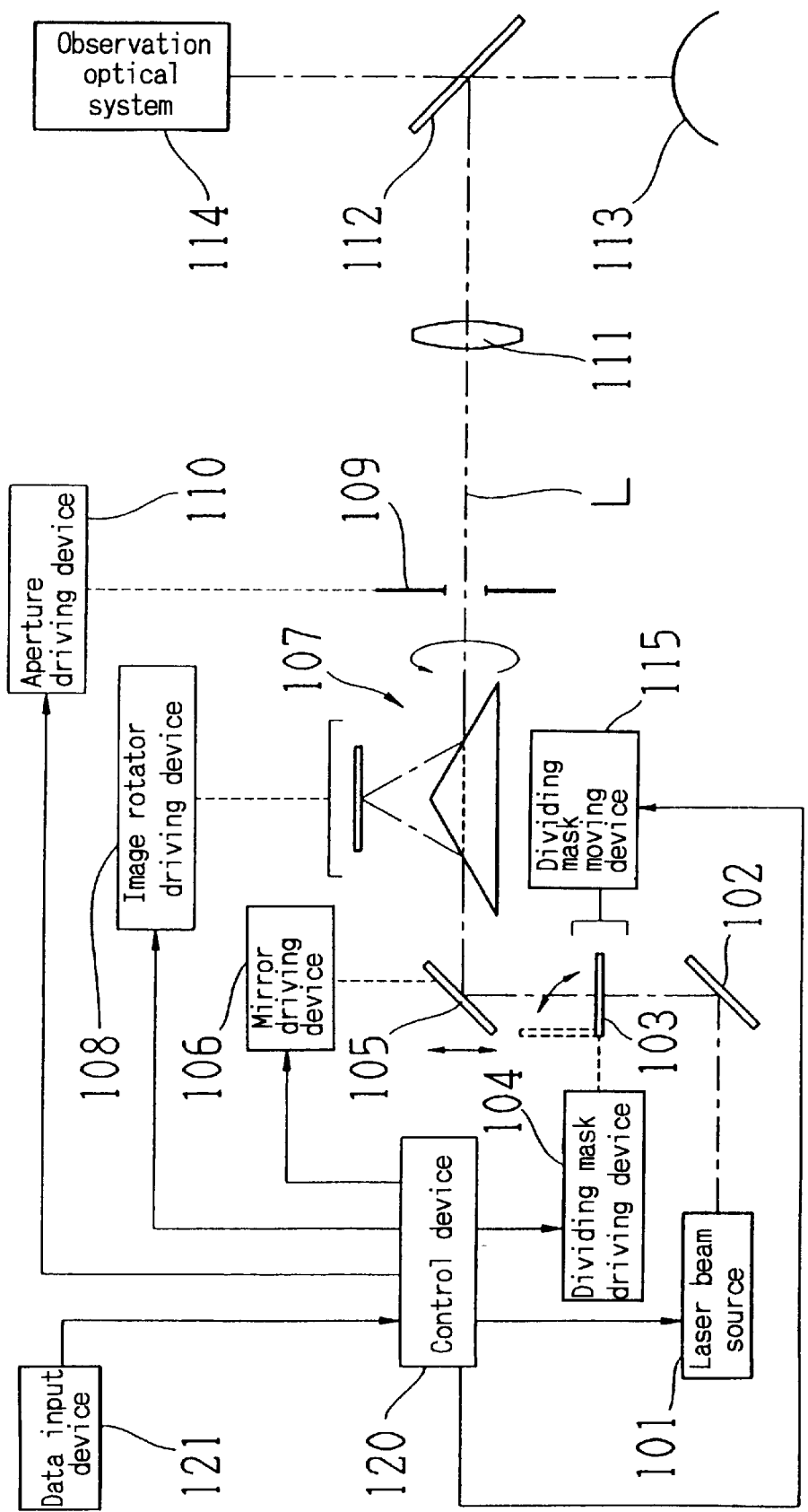
FIG. 10 is a view showing a schematic arrangement of an optical system and a control system provided for an apparatus for operating upon a cornea.

An examples of the apparatus 90 is disclosed by Japanese Patent Publication Laid-Open No. HEI9(1997)-266925 corresponding to U.S. patent application Ser. No. 09/013,884 and DE publication No. 19703661. FIG. 10 is a view showing a schematic arrangement of an optical system and a control system provided for the apparatus 90. In FIG. 10, 103 denotes a dividing mask having a plurality of a strip shape mask which forms a line. A dividing mask driving device 104 shuts and opens the strip shaped masks, then a long direction of an excimer laser in the form of a thin rectangle shape, from a laser beam source 101, is partially cut. A laser beam passing through the mask is scanned by a plane mirror 105, thereby the laser beam being moved and selectively limited. Accordingly, the cornea 113 is irradiated with the limited laser beam via a delivering optical system. A control device 120 determines a coordinate position of the cornea 113 to which a laser beam irradiation is given, a number of pulses of the laser irradiation at the coordinate position, and an irradiation power thereat, based on the amount of corneal ablation inputted by a data input device 121. The control device 120 then controls the laser source 101, a dividing mask driving device 104 for the dividing mask 103, a mirror driving device 106 for the plane mirror 105, an image rotator driving device 108 for an image rotator 107, and an aperture driving device 110 for an aperture 109, thereby performing an laser beam irradiation. Accordingly, the corneal surface is ablated so as to be a non-spherical shape based on the data of the amount of corneal ablation.

In above description, such embodiment is disclosed that distribution information of the objective refractive power and distribution information of the corneal surface refractive power (distribution of a corneal curvature) are utilized for surgery for correcting upon a cornea. Alternatively, a modification may be utilized as following.

In the case of diagnosis, if distribution information of the objective refractive power is compared with distribution information of the corneal surface refractive power, then it can be distinguished quantitatively or qualitatively whether an astigmatism component of the eye is caused by the corneal shape or a factor of an intraocular component existing from a back position of a corneal surface to a retina. That is, by subtracting the refractive power at a central position from the equivalent emmetropia corneal surface refractive power at any position, distribution of the astigmatism component (a residual astigmatism) of the eye, existing over the retina exclusive of the corneal surface, can be calculated. This result is displayed on the display 56 in the form of a color map shown in FIG. 7. Referring to this color map, suitability of a contact lens which is used for correcting ametropia can be determined. For example, in the case of irregular astigmatism (this case can be known from distribution information of the objective refractive power), prescription for spectacles and that for a soft contact lens are not enough to correct a visual acuity. However, if irregular astigmatism proves to be mainly caused by the corneal surface shape, then the ophthalmologist can recommend a patient to use a hard contact lens for correcting a visual acuity. Further, in the case of inserting an intraocular lens for treating cataract, the color map displayed on the display 56 can be utilized as information in order to prohibit astigmatism from being induced due to inclination at the time of the insertion.

The present invention may be made by several modifications. For example, a measuring device for obtaining an objective refractive power may be separated from a measuring device for obtaining a corneal shape. In this case, it may be configured so that respective measured data may be inputted into a personal computer, then the personal computer may perform an analysis and display its result. Alternatively, it may be configured so that the analysis may be performed by only one measuring apparatus provided separately.

In addition, in the preferred embodiment, a corneal shape measurement by using a placido ring projection is adopted as an example. The present invention is not restricted to this preferred embodiment, thus being applied to all kinds of corneal shape measurement apparatus capable of obtaining a corneal curvature and a 3-D shape of a cornea, and all kinds of objective refractive power measurement apparatus, based on the principle or the method by which distribution of an objective refractive power can be obtained.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus for calculating ophthalmic information of an eye to be operated, then determining an amount of corneal ablation for use in surgery for correcting ametropia, based on the calculated ophthalmic information, the apparatus comprising:

a first input device for inputting data of a pre-operative corneal shape obtained by corneal shape measurement;

a second input device for inputting data of pre-operative refractive power obtained by objective refractive power measurement;

a first calculating device for calculating data of equivalent emmetropia corneal surface refractive power which is equivalent to cause the eye to be emmetropia, based on the data of the corneal shape inputted by the first input device and the data of the refractive power inputted by the second input device;

a second calculating device for calculating estimation data of a post-operative corneal shape, based on the data of the equivalent emmetropia corneal surface refractive power calculated by the first calculating device;

a third calculating device for calculating data of the amount of corneal ablation, based on the data of the corneal shape inputted by the first input device and the data of the corneal shape calculated by the second calculating device; and a display device for displaying at least one of results calculated by the first, second and third calculating devices.

2. The ophthalmic apparatus according to claim 1, wherein the first input device is for inputting distribution data of a pre-operative corneal curvature;

the second input device is for inputting distribution data of the pre-operative refractive power;

the first calculating device converts the distribution data of the corneal curvature into distribution data of corneal surface refractive power, based on the Snell's law, then calculates distribution data of the equivalent emmetropia corneal surface refractive power in a manner of adding the distribution data of the corneal surface refractive power and the distribution data of the refractive power;

the second calculating device converts the distribution data of the equivalent emmetropia corneal surface refractive power into distribution data of a corneal curvature, based on the Snell's law; and the third calculating device calculates distribution data of the amount of corneal ablation, based on the distribution data of the corneal curvature inputted by the first input device and the distribution data of the corneal curvature calculated by the second calculating device.

3. The ophthalmic apparatus according to claim 1, wherein the first input device is for inputting distribution data of pre-operative corneal surface refractive power;

the second input device is for inputting distribution data of the pre-operative refractive power;

the first calculating device calculates distribution data of the equivalent emmetropia corneal surface refractive power in a manner of adding the distribution data of the corneal surface refractive power and the distribution data of the refractive power;

the second calculating device converts the distribution data of the equivalent emmetropia corneal surface refractive power into distribution data of a corneal curvature, based on the Snell's law; and the third calculating device converts the distribution data of the corneal surface refractive power inputted by the first input device into distribution data of a corneal curvature, based on the Snell's law, then calculates distribution data of the amount of corneal ablation, based on the converted distribution data of the corneal curvature and the distribution data of the corneal curvature calculated by the second calculating device.

4. The ophthalmic apparatus according to claim 1, wherein the third calculating device calculates a 3-D shape of a cornea based on the data of the corneal shape inputted by the first input device and a 3-D shape of the cornea based on the data of the corneal shape calculated by the second calculating device, then calculates the data of the amount of corneal ablation based on difference between both 3-D shapes with defining a corneal center as standard.

5. The ophthalmic apparatus according to claim 1, wherein the first input device is for inputting either data of a pre-operative corneal curvature or data of pre-operative corneal surface refractive power;

the display device displays at least one between data of corneal surface refractive power obtained from the inputted data of the corneal curvature or the inputted data of the corneal surface refractive power and the data of the refractive power inputted by the second input device, and the data of the equivalent emmetropia corneal surface refractive power calculated by the first calculating device on the identical display graphically.

6. The ophthalmic apparatus according to claim 1, wherein the display device displays graphically at least one of a corneal shape obtained from the data of the corneal shape inputted by the first input device, a corneal shape obtained from the data of the corneal shape calculated by the second calculating device and a difference shape between both corneal shapes.

7. An ophthalmic apparatus for calculating ophthalmic information, the apparatus comprising:

an input device for inputting data of corneal surface refractive power obtained by corneal shape measurement and data of refractive power obtained by objective refractive power measurement;

a calculating device for calculating data of equivalent emmetropia corneal surface refractive power which is equivalent to cause the eye to be emmetropia in a manner of adding the data of the corneal surface refractive power and the data of the refractive power, both data being inputted by the input device; and a display device for displaying a result calculated by the calculating device.

8. The ophthalmic apparatus according to claim 7, wherein the display device displays graphically at least one between the data of the corneal surface refractive power and the data of the refractive power, and the data of the equivalent emmetropia corneal surface refractive power on the identical display.

9. The ophthalmic apparatus according to claim 7, wherein the data of the corneal surface refractive power is distribution data of the corneal surface refractive power obtained from a corneal shape obtained by measuring a corneal region extending from a center to a periphery;

the data of the refractive power is distribution data of the refractive power obtained by measuring refractive power objectively, which varies in a meridian direction on a cornea and in a direction from a center to a periphery;

the calculating device calculates distribution data of the equivalent emmetropia corneal surface refractive power in a manner of associating both distribution data on the cornea with each other.

10. The ophthalmic apparatus according to claim 9, wherein the distribution data of the corneal surface refractive power is distribution of refractive power at respective entering positions on the cornea at the time when an infinite light bundle enters into the cornea from a direction in front of the eye, the distribution data is calculated based on the Snell's law.

11. The ophthalmic apparatus according to claim 9, further comprising:

a second calculating device for converting the distribution data of the equivalent emmetropia corneal surface refractive power into distribution data of a corneal curvature, based on the Snell's law; and a second display device for displaying graphically a corneal shape based on the distribution data of the corneal curvature calculated by the second calculating device and a corneal shape obtained by the corneal shape measurement on the identical display.

12. The ophthalmic apparatus according to claim 9, further comprising:

a second calculating device for calculating distribution data of residual astigmatism exclusive of corneal surface astigmatism, based on the distribution data of the equivalent emmetropia corneal surface refractive power; and a second display device for displaying a result calculated by the second calculating device.

13. The ophthalmic apparatus according to claim 7, further comprising at least one of:

a corneal shape measuring device which performs the corneal shape measurement in order to obtain the data of the corneal surface refractive power; and a refractive power measuring device which performs the objective refractive power measurement in order to obtain the data of the refractive power.

14. An ophthalmic apparatus for determining an amount of corneal ablation for use in surgery for correcting ametropia in a manner of ablating a cornea, the apparatus comprising:

a first input device for inputting distribution data of a pre-operative corneal curvature obtained by corneal shape measurement;

a second input device for inputting distribution data of pre-operative refractive power obtained by objective refractive power measurement; and an ablation amount calculating device for calculating data of the amount of corneal ablation, based on the distribution data of the corneal curvature inputted by the first input device and the distribution data of the refractive power inputted by the second input device.

15. The ophthalmic apparatus according to claim 14, wherein the ablation amount calculating device comprises:
   a first calculating device for calculating distribution data of equivalent emmetropia corneal surface refractive power which is equivalent to cause the eye to be emmetropia, based on the distribution data of the corneal curvature inputted by the first input device and the distribution data of the refractive power inputted by the second input device;
   a second calculating device for calculating estimation distribution data of a post-operative corneal curvature, based on the distribution data of the equivalent emmetropia corneal surface refractive power calculated by the first calculating device; and
   a third calculating device for calculating distribution data of the amount of corneal ablation, based on the distribution data of the corneal curvature inputted by the first input device and the distribution data of the corneal curvature calculated by the second calculating device.

16. The ophthalmic apparatus according to claim 15, wherein the first calculating device converts the distribution data of the corneal curvature inputted by the first input device into distribution data of corneal surface refractive power, based on the Snell's law, then calculates the distribution data of the equivalent emmetropia corneal surface refractive power in a manner of adding the converted distribution data of the corneal surface refractive power and the distribution data of the refractive power.

17. The ophthalmic apparatus according to claim 15, the second calculating device converts the distribution data of the equivalent emmetropia corneal surface refractive power into the distribution data of the corneal curvature, based on the Snell's law.

18. The ophthalmic apparatus according to claim 15, wherein the third calculating device calculates a 3-D shape of the cornea based on the distribution data of the corneal curvature inputted by the first input device and a 3-D shape of the cornea based on the distribution data of the corneal curvature calculated by the second calculating device, then calculating the distribution data of the amount of corneal ablation based on difference between both 3-D shapes with defining a corneal center as standard.

19. The ophthalmic apparatus according to claim 15, further comprising:
   a display device for displaying graphically at least one of a corneal shape obtained from the distribution data of the corneal curvature inputted by the first input device, a corneal shape obtained from the distribution data of the corneal curvature calculated by the second calculating device and a difference shape between both corneal shapes.

20. The ophthalmic apparatus according to claim 14, further comprising:
   a transfer device for transferring the data of the amount of corneal ablation, calculated by the ablation amount calculating device, to surgery apparatus for ablating the cornea with a laser beam.

21. The ophthalmic apparatus according to claim 14, further comprising at least one of:
   a corneal shape measuring device which performs the corneal shape measurement in order to obtain the distribution data of the corneal curvature; and
   a refractive power measuring device which performs the objective refractive power measurement in order to obtain the distribution data of the refractive power.

22. An ophthalmic apparatus for determining an amount of corneal ablation for use in surgery for correcting ametropia in a manner of ablating a cornea, the apparatus comprising:
   an input device for inputting data of a pre-operative corneal curvature obtained by corneal shape measurement and data of pre-operative refractive power obtained by refractive power measurement; and
   a calculating device for calculating data of the amount of corneal ablation, which causes a corneal surface to be non-spherical shape such that influence of aberration is eliminated, based on the data inputted by the input device.

23. An ophthalmic apparatus utilized for surgery for correcting ametropia in a manner of ablating a cornea, the apparatus comprising:
   a first input device for inputting distribution data of a pre-operative corneal curvature, obtained by corneal shape measurement;
   a second input device for inputting distribution data of pre-operative refractive power, obtained by objective refractive power measurement;
   a calculating device for calculating data of an amount of corneal ablation, based on the distribution data of the corneal curvature inputted by the first input device and the distribution data of the refractive power inputted by the second input device; and
   an ablation device for ablating the cornea with a laser beam, based on the data of the amount of corneal ablation calculated by the calculating device.

24. An ophthalmic apparatus utilized for surgery for correcting ametropia in a manner of ablating a cornea, the apparatus comprising:
   an input device for inputting data of a pre-operative corneal shape obtained by corneal shape measurement and data of pre-operative refractive power obtained by refractive power measurement;
   a calculating device for calculating data of an amount of corneal ablation, which causes a corneal surface to be non-spherical shape such that influence of aberration is eliminated, based on the data inputted by the input device; and
   an ablation device for ablating the cornea with a laser beam, based on the data of the amount of corneal ablation calculated by the calculating device.

* * * * *